United States Patent [19]

Gästrin

[11] Patent Number: 4,675,888
[45] Date of Patent: Jun. 23, 1987

[54] PATIENT SUPPORT SYSTEM IN A NARROW-BEAM TOMOGRAPHIC IMAGING APPARATUS

[75] Inventor: Jan Gästrin, Espoo, Finland

[73] Assignee: Instrumentarium Corp., Finland

[21] Appl. No.: 688,260

[22] Filed: Jan. 2, 1985

[30] Foreign Application Priority Data

Jan. 6, 1984 [FI] Finland .................................. 840044

[51] Int. Cl.⁴ .............................................. A61B 6/14
[52] U.S. Cl. ..................................... 378/38; 378/39; 378/40
[58] Field of Search ................... 378/38–40, 378/208

[56] References Cited

U.S. PATENT DOCUMENTS 3,743,832 7/1973 Wright ................................... 378/40
4,044,265 8/1977 Schmidt ............................. 378/208
4,242,585 12/1980 Yamano ................................. 378/39

FOREIGN PATENT DOCUMENTS 0309701 7/1971 U.S.S.R. ............................... 378/208

Primary Examiner—Janice A. Howell
Attorney, Agent, or Firm—Andrus, Sceales, Starke & Sawall

[57] ABSTRACT

The invention relates to a patient support system in a narrow-beam tomographic X-ray apparatus, having a fixed frame fitted with a substantially vertical member (1), means (7, 8, 9) mounted on the frame for supporting a patient's head, said means being adapted to hold a patient's head (P) steady during the imaging session, as well as a bearer bar (3), fitted with a source of X-radiation (4) and imaging instruments (5) on the opposite sides relative to an object to be imaged and said bar being adapted in a known manner to perform rotational or combined rotational linear movement for scanning a predetermined layer to be imaged. In order to facilitate patient positioning and to secure proper positioning of a patient, said head support means (7, 8, 9) are set in a manner that the medial sagittal plane (S) of a patient supported thereby does not intersect said vertical frame member (1).

2 Claims, 5 Drawing Figures

PATIENT SUPPORT SYSTEM IN A NARROW-BEAM TOMOGRAPHIC IMAGING APPARATUS

The present invention relates to a patient support system in a narrow-beam tomographic X-ray apparatus.

BACKGROUND OF THE INVENTION

Patient positioning in clinical work has been found the most difficult subdomain in dental narrow-beam tomography. When considering the actual imaging occasion, thus ignoring the development of film, an incorrect patient positioning is the most common reason for having to do a retake and thus for unnecessary increase of a radiation dose that a patient is exposed to. Approximately, as much as up to 20% of images must be retaken as a result of incorrect patient positioning. Thus, all efforts intended for securing a patient position and simplification of patient positioning will be to the benefit of a patient in the form of a decreased radiation dose.

Patient positioning and determination of the position of a patient are significantly based on the evaluation of the position and location of the head, neck and shoulders of a patient. In the patient positioning involved in dental imaging, a primary objective is the positioning of a patient in the imaging apparatus symmetrically in a manner that, on one hand, the front and molar teeth and, on the other hand, both upper jaw and lower jaw teeth can be positioned at the sharply imaged layer. Furthermore, the plane of occlusion is set horizontal, the neck column is straightened, the patient is positioned to lean slightly backward and his or her shoulders are pressed as low as possible. It is necessary to make compromises between various objectives with patients in general and especially with asymmetric patients.

The general instruments in patient positioning include an occlusion brace for setting the upper and lower jaw teeth in the same plane, a chin brace, a forehead brace, temple braces, handgrip means as well as various light lines focused on the face of a patient. However, no final solution to the problems of patient positioning has been found and no support systems or light lines can make sure of a successful patient positioning without the judgement and consideration of an operator. The reliability of judgement is substantially improved if positioning is easy to perform and the operator is able to see the face of a patient as clearly as possible. Essential in the judgement of symmetry is that the operator sees the patient directly from the front.

The instruments are intended for the use of a dentist employee in either the standing or sitting patient position. In general, an apparatus designed for a standing patient can also be used for a sitting patient position by fitting it with a regular chair. The equipment intended for hospital use can also employ a lying patient position. In the prior art equipment employing a standing patient position, the patient is directly facing the support column of said apparatus, i.e. the component that carries imaging equipment and patient positioning instruments. For reasons of saving space, the support column is usually set by a wall so the patient, almost without exception, is also facing the wall. Nearly all such instruments are provided with a mirror for the operator to see the face of a patient. Through an inclined mirror, however, it is impossible to obtain a symmetric viewing angle to the face of a patient. Due to mutual differences in the heights of an operator and patient, all the operator often can see in the mirror is just the forehead or arm of a patient instead of his or her whole face.

In the above-described equipment it is generally possible to use a patient chair and, thus, a sitting patient positioning. However, the knees of a grown-up patient will then without exception hit the column and, as positioned to flank said column, the knees will be in the way of an operator. The same applies also to the equipment totally based on a sitting patient position and in which a patient is facing the column. In such equipment, the plane of examination of an operator lies considerably higher than the face of a patient and, thus, all that is visible in the mirror are the arms of a patient.

In the prior art equipment employing a sitting patient position and in which a patient is facing away from the column and wall, the above problems of seeing a patient do not occur. However, the patient support equipment, chin and temple braces, must be turned aside when a patient is placed in the device and correspondingly when he or she is leaving the device. These devices are not fitted with a forehead brace either, which is one of the most critical components for reliable patient positioning. Furthermore, in these devices, the X-ray tube passes between the column and patient which is why the patient must be brought further away from the column. As a result, such equipment requires more space.

SUMMARY OF THE INVENTION

An object of the invention is to provide, for narrow-beam tomographic X-ray equipment, a patient support system in which the above-described prior art drawbacks are eliminated as thoroughly as possible. A particular object of the invention is to provide a support system which facilitates a simple treatment of a patient and positioning and supporting of a patient in the imaging apparatus in a manner that the number of incorrect pictures and resulting retakes can be minimized. An object is also to decrease the space requirement of such apparatus.

These objects of the invention are achieved by arranging the head support means in a manner such that a patient lies transversely with respect to the support column or vertical frame member of the apparatus. The operator can see the face of a patient directly from the front which substantially facilitates patient positioning. Placing a patient in the device and out of it is also simple. Furthermore, the rest position of a turnable imaging equipment support arm can be made nearly in the direction of the arm support equipment, so the apparatus won't require a lot of space. Also the use of a chair mounted on the apparatus for a sitting patient position is simple and convenient.

DESCRIPTION OF THE DRAWINGS

The invention will now be described in more detail with reference made to the accompanying drawing, in which.

DESCRIPTION OF THE PREFERRED EMBODIMENT

Figure 1:
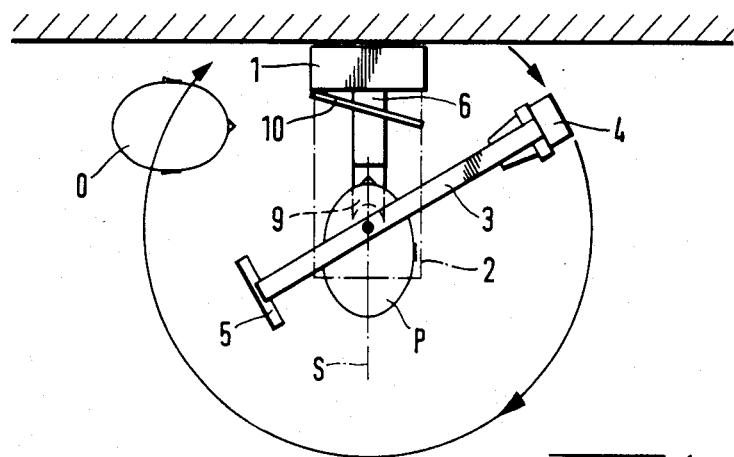
FIGS. 1 and 2 show prior art systems in principle.

Referring to the drawing, reference numeral 1 designates an imaging apparatus support column which provides a fixed vertical body for the apparatus. Support column 1 is provided with a first horizontal member 2 to which is pivotably attached a bearer bar 3, whose opposite ends are fitted with an X-ray tube 4 and a film cassette 5 with its mountings and shifting means, not shown in detail. Bearer bar 3, together with its imaging gear, can be adapted in a per se known manner to perform linear or combined linear-circular motion. As shown in FIG. 5, said member 2 carries equipment for supporting the upper head portion of a patient P to be imaged, said equipment including a forehead brace 7 and temple braces 8. Support column 1 is fitted with another horizontal member 6 which is provided with a chin brace 9 for patient P. The medial sagittal plane of a patient is indicated by S. An imaging apparatus operator O is in FIGS. 1-4 positioned in the spot relative to the apparatus and patient, which in terms of patient positioning is the most critical and typical. In the figures, the appratus is shown in a position by the wall, which in practice is the most common solution for space saving reasons.

In the most common prior art solution shown in FIG. 1, a patient P is placed in the apparatus to face the support column 1. The operator O can only see the face of a patient from the front by means of a mirror 10. Therefore, and because the patient and operator are often of different heights (e.g. men, women, children), it is difficult to position a patient precisely in a spot sharply imaged by the apparatus, so that a given rather thin layer of e.g. a set of teeth can be imaged on the film according to narrow-beam tomographic technique.

Figure 2:
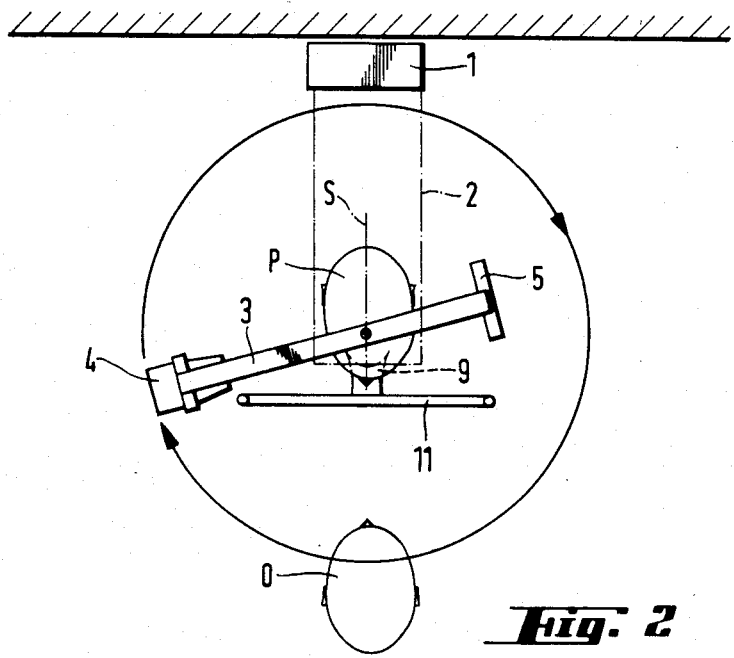

On the other hand, in the prior art solution shown in FIG. 2, a patient faces directly away from the support column. It is true that the operator can now see the face of a patient but bracing the patient's head is troublesome. In practice, a patient is often in a sitting position, the chair (not shown in the figure) being fitted with support members 11, mounted on the armrests and provided with a chin brace 9. Thus, placing a patient in the apparatus is inconvenient as it is necessary to circle around the head support gear or it must be pivoted aside. The apparatus also requires quite a lot of space, as pointed out above.

Figure 3:
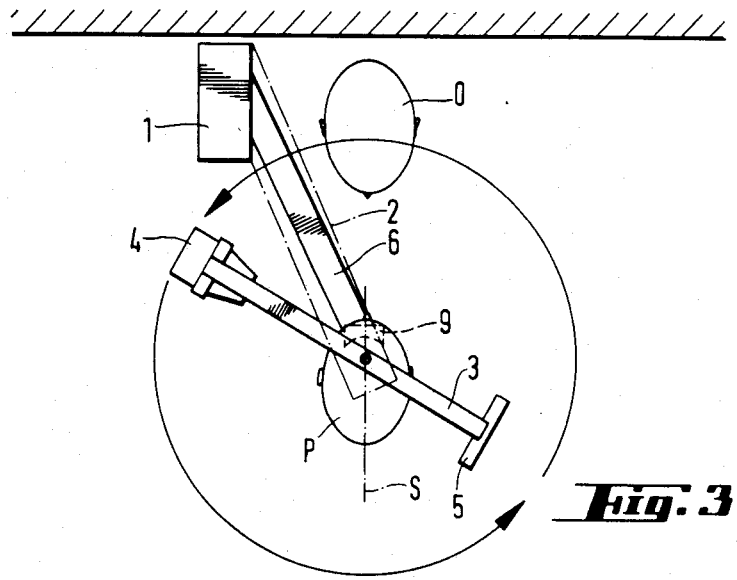
FIGS. 3 and 4 show in principle two embodiments based on the invention.
Figure 4:
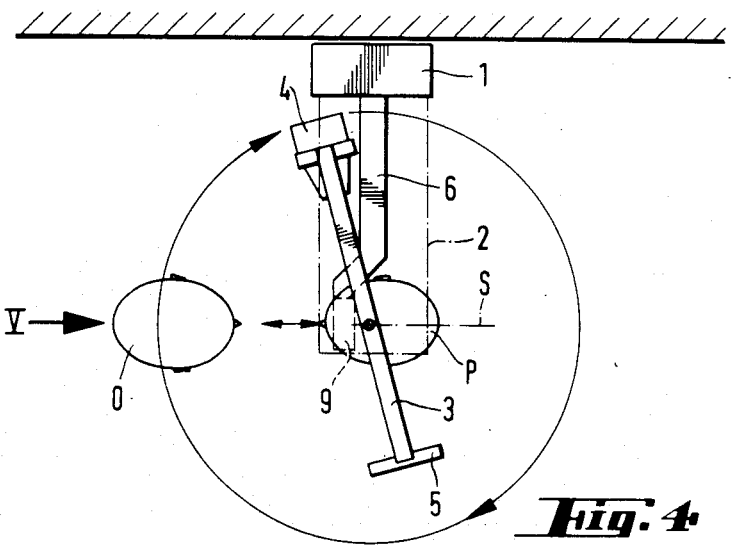
Figure 5:
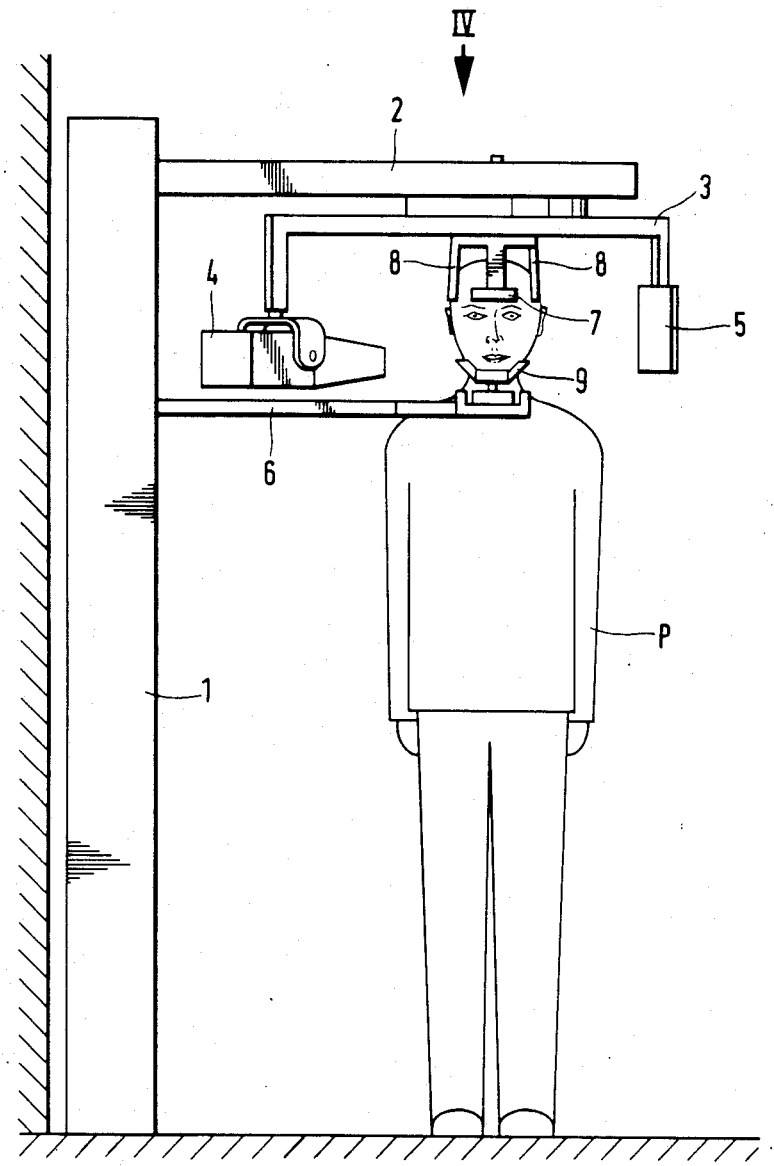
FIG. 5 is a side view of the embodiment of FIG. 4.

FIGS. 3 and 4 illustrate some embodiments of the invention which differ from each other mainly in the way the horizontal members 2 and 6 of support column 1 are mounted relative to the support column. It is obvious that bracing of members 2 and 6 can be effected in a plurality of ways and positions. Such members can also form a certain angle relative to each other and be designed in various ways. In addition, they can be mounted on a separate slide unit etc., vertically movable relative to support column 1. What is essential about the invention is that the head support gear is mounted in a manner that a patient is positioned transversely relative to the support column. Thus, all necessary head support means are readily mountable on the support column and its horizontal members. Placing a patient in the imaging apparatus is also easy, no matter whether the patient is sitting or standing. Also important is that the operator can see the patient's face directly from the front. By also using a chin brace 9, adjustable in the direction of the patient's medial sagittal plane S, and forehead and temple braces 7 and 8 (see FIG. 5), it is possible to eliminate as effectively as possible the imaging errors and the associated retakes, resulting from the incorrect positioning of a patient. The apparatus is also preferable in terms of space utilization since, in its rest position, said bearer bar 3 extends substantially parallel to support column members 2 and 6.

The invention is not limited to the above embodiments but a plurality of modifications are conceivable within the scope of the annexed claims.

I claim:

1. A patient support system for a narrow beam tomographic X-ray apparatus for obtaining tomographic X-ray images of the jaw area of a patient, said support system comprising:
   a substantially vertical support member (1) for mounting the system on the floor or wall of a building;
   a first substantially horizontal upper frame member (2) extending from said vertical support member;
   a pair of spaced temple braces (8) mounted on said first frame member to depend therefrom, said temple braces being so mounted on said first frame member that the perpendicular bisecting plane of a line extending between said spaced temple braces avoids intersection with said vertical support member;
   a forehead brace (7) mounted on said first frame member to depend therefrom, said forehead brace being mounted on said first frame member to be generally in said perpendicular bisecting plane of said spaced temple braces;
   a bearer bar (3) having a source of X-ray radiation (4) at one end and an imaging medium (5) at the other end, said bearer bar depending from said first frame member and being movably mounted thereon for imaging a predetermined layer of the jaw area of the patient;
   a second substantially horizontal lower frame member (6) extending from said vertical support member spacedly below said first frame member; and
   a chin brace (9) mounted on said second frame member to lie generally in alignment with said forehead brace and along said perpendicular bisecting plane of said spaced temple braces;
   so that said forehead and temple braces and said chin brace orient the head of the patient such that the medial sagittal plane (5) of the patient's head does not intersect said vertical support member during tomographic imaging of the jaw area, said X-ray radiation source and said imaging medium being positionable on opposite sides of the patient's head when the patient's head is received in said braces.

2. A support system as set forth in claim 1, characterized in that said chin brace (9) is adjustably mounted on said second frame member (6).

* * * * *